United States Patent
Ogawa

(10) Patent No.: US 9,738,586 B2
(45) Date of Patent: Aug. 22, 2017

(54) VACUUM DISTILLATION METHOD FOR EASILY POLYMERIZABLE COMPOUND AND METHOD FOR PRODUCING ACRYLIC ACID

(71) Applicant: Mitsubishi Chemical Corporation, Chiyoda-ku (JP)

(72) Inventor: Yasushi Ogawa, Yokkaichi (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/134,980

(22) Filed: Apr. 21, 2016

(65) Prior Publication Data

US 2016/0237017 A1 Aug. 18, 2016

Related U.S. Application Data

(63) Continuation of application No. PCT/JP2014/078603, filed on Oct. 28, 2014.

(30) Foreign Application Priority Data

Oct. 29, 2013 (JP) .................................. 2013-224082

(51) Int. Cl.
C07C 51/44 (2006.01)
F04F 5/20 (2006.01)
B01D 3/10 (2006.01)
B01D 3/38 (2006.01)

(52) U.S. Cl.
CPC .............. *C07C 51/445* (2013.01); *B01D 3/10* (2013.01); *B01D 3/38* (2013.01); *F04F 5/20* (2013.01)

(58) Field of Classification Search
CPC . C07C 51/445; B01D 3/38; B01D 3/10; F04F 5/20
See application file for complete search history.

(56) References Cited

U.S. PATENT DOCUMENTS

| | | | |
|---|---|---|---|
| 3,702,346 A | 11/1972 | Kellar | |
| 6,739,288 B1 * | 5/2004 | Kumamoto | B01J 19/0013 122/15.1 |
| 6,878,239 B1 | 4/2005 | Matsumoto et al. | |
| 8,932,434 B2 * | 1/2015 | Lee | B01D 3/14 202/158 |
| 2004/0222077 A1 | 11/2004 | Yada et al. | |
| 2007/0060703 A1 | 3/2007 | Ogawa et al. | |
| 2007/0173667 A1 | 7/2007 | Sakai et al. | |
| 2008/0228003 A1 | 9/2008 | Ogawa et al. | |

FOREIGN PATENT DOCUMENTS

| | | |
|---|---|---|
| CN | 1276363 A | 12/2000 |
| CN | 1561251 A | 1/2005 |
| EP | 1 057 804 A2 | 12/2000 |
| EP | 1 731 496 A1 | 12/2006 |
| JP | 1-105000 | 4/1989 |
| JP | 10-204030 A * | 8/1998 |
| JP | 2000-256221 | 9/2000 |
| JP | 2000-344711 | 12/2000 |
| JP | 2005-289927 | 10/2005 |
| JP | 2007-217401 | 8/2007 |
| JP | 2007-255805 | 10/2007 |
| JP | 4095471 | 6/2008 |
| JP | 2009-149587 | 7/2009 |
| WO | WO 03/018162 A1 | 3/2003 |
| WO | WO 2005/100295 A1 | 10/2005 |

OTHER PUBLICATIONS

English Translation of International Search Report issued Jan. 20, 2015 in PCT/JP2014/078603, filed Oct. 28, 2014.
Third Party Observation submitted Nov. 10, 2015 in PCT/JP2014/078603, filed Oct. 28, 2014.
"Catalogue of Steam Ejectors Single and Multistage", Japan Ejector Engineering Co., Ltd., 1998, 19 pages (with partial English Translation).
"Catalogue of Liquid Sealed Vacuum Pump/Compressor", Awamura Manufacturing Co., Ltd. 1998, 18 pages (with partial English Translation).
English translation of International Preliminary Report on Patentability and Written Opinion issued May 12, 2016 in PCT/JP2014/078603.
Extended European Search Report issued Oct. 11. 2016 in Patent Application No. 14857447.8.
Combined Chinese Office Action and Search Report issued Oct. 10. 2016 in patent application No. 201480059285.4 with unedited computer generated English translation.
Chinese Office Action dated Apr. 28, 2017, in Chinese Patent Application No. 201480059285.4 (with English Translation).

* cited by examiner

*Primary Examiner* — Paul A Zucker
(74) *Attorney, Agent, or Firm* — Oblon, McClelland, Maier & Neustadt, L.L.P.

(57) ABSTRACT

An object of the present invention is to provide a method in which, when a steam ejector is used as a decompression apparatus for a vacuum distillation process for an easily polymerizable compound, the steam ejector is prevented from being occluded due to polymerization of the easily polymerizable compound. Another object of the present invention is to provide a method for manufacturing an acrylic acid that is an easily polymerizable compound, using the above-described method. The above object is accomplished by a method for manufacturing an acrylic acid, which comprises a step of executing vacuum distillation, using a steam ejector, on an acrylic acid resulting from gas-phase catalytic oxidation using propane, propylene, or acrolein as a material, wherein the vacuum distillation step includes a step of heating an outer surface of the steam ejector.

20 Claims, 3 Drawing Sheets

VACUUM DISTILLATION METHOD FOR EASILY POLYMERIZABLE COMPOUND AND METHOD FOR PRODUCING ACRYLIC ACID

CROSS-REFERENCE TO RELATED APPLICATION

This is a continuation of International Application PCT/JP2014/078603, filed on Oct. 28, 2014, designated the U.S., claims priority from Japanese Patent Application 2013-224082 which was filed on Oct. 29, 2013, and the entire contents of which are incorporated herein by reference.

TECHNICAL FIELD

The present invention relates to a method for vacuum distillation of an easily polymerizable compound and a method for manufacturing an acrylic acid. More specifically, the present invention relates to a method for vacuum distillation of an easily polymerizable compound in which a steam ejector is used as a decompression apparatus and in which the easily polymerizable compound is prevented from being polymerized inside the steam ejector. The present invention also relates to a method for manufacturing an acrylic acid that is an easily polymerizable compound, using the above-described method.

BACKGROUND ART

As a method for manufacturing an acrylic acid, a method is commonly known which involves collecting, in a collection solvent such as water, an acrylic-acid-containing gas resulting from gas-phase catalytic oxidation using propane, propylene or acrolein as a material, separating an acrylic acid from the resultant acrylic acid solution, and purifying the separated acrylic acid by vacuum distillation.

Furthermore, as a method for manufacturing an acrylic ester, for example, a method is known which involves causing esterification between a purified acrylic acid and alcohol to obtain a crude acrylic ester and distilling and purifying the crude acrylic ester, or causing transesterification between an acrylic ester and alcohol to obtain a crude acrylic ester and distilling and purifying the resultant crude acrylic ester.

Acrylic acids are easily polymerizable compounds. Polymerization is likely to occur in a purification process for a solution of acrylic acids, particularly a distillation process involving a large amount of heating. Thus, to prevent polymerization of acrylic acids in a distillation column, a method is used which involves supplying a polymerization inhibitor or molecular oxygen or decompressing the inside of the distillation column in order to reduce the temperature in the distillation column.

Distilled gas from the distillation column is cooled and condensed by a heat exchanger, and a portion of uncondensed gas is sucked into a decompression apparatus. As the decompression apparatus, a liquid seal vacuum pump or a steam ejector is commonly used. However, the uncondensed gas also contains an acrylic acid, and thus, polymerization of the acrylic acid may occur around the decompression apparatus.

Patent Literature 1 (Japanese Patent Application Laid-open No. 2000-344711) discloses a method in which, in the above-described case, the gas sucked into the steam ejector is discharged from the steam ejector along with driving steam and in which, during the subsequent cooling, a polymerization-inhibitor-containing liquid is supplied.

Furthermore, Patent Literature 2 (Japanese Patent Application Laid-open No. 2005-289927) discloses a method in which the steam and the sucked gas discharged from the steam ejector are cooled to lower than 40° C. with no addition of a polymerization inhibitor to prevent polymerization of the acrylic acid in the condensed liquid.

CITATION LIST

Patent Literatures

Patent Literature 1: Japanese Patent Application Laid-open No. 2000-344711
Patent Literature 2: Japanese Patent Application Laid-open No. 2005-289927

SUMMARY OF INVENTION

Technical Problem

However, the inventions described in Patent Literature 1 and Patent Literature 2 use the steam ejectors but use the method of preventing polymerization of the easily polymerizable compound by addition of the polymerization inhibitor or by cooling. The inventions do not perform a special operation on the steam ejector in order to prevent polymerization of the easily polymerizable compound. Thus, if the reduced pressure fails to be maintained due to occlusion of the steam ejector, the distillation column needs to be shut down.

The steam ejector is a small piece of equipment, and when occluded, is switched to a spare to allow shutdown of the distillation column to be avoided. However, a fluctuation in pressure that occurs at the time of the switching disturbs flows of the gas and the liquid in the distillation column, triggering polymerization and occlusion in the distillation column. Furthermore, disadvantageously, a heavy burden on operators has been involved in cleaning of an occluded area, dismantling and recovery, and the like. Consequently, an essential solution is desired.

The present invention has been developed to solve the above-described problems. That is, an object of the present invention is to provide a method in which, when a steam ejector is used as a decompression apparatus for a vacuum distillation process for an easily polymerizable compound, the steam ejector is prevented from being occluded due to polymerization of the easily polymerizable compound. Further an object of the present invention is to provide a method for manufacturing an acrylic acid that is an easily polymerizable compound, using the above-described method.

Solution to Problem

Upon heating an outer surface of a steam ejector, the present inventor found that, contrary to the inventor's expectations, the heating serves to suppress generation of polymers. As a result of earnest studies based on this fact, the present inventor has found that, when an easily polymerizable compound is subjected to vacuum distillation using the steam ejector, polymers are reliably prevented from adhering to the inside of the steam ejector by heating the outer surface of the steam ejector. Thus, the present invention has been completed.

A first invention of the present invention is a method for manufacturing an acrylic acid, which comprises a step of executing vacuum distillation, using a steam ejector, on an acrylic acid resulting from gas-phase catalytic oxidation using propane, propylene, or acrolein as a material, wherein the vacuum distillation step includes a step of heating an outer surface of the steam ejector.

The outer surface of the steam ejector in the first invention is preferably heated using a steam trace and is preferably heated using an electro-thermal heater.

Furthermore, the outer surface of the steam ejector is preferably heated to 50° C. or higher.

Furthermore, the steam ejector preferably has a multistage configuration, and a liquid seal vacuum pump is preferably arranged downstream of the steam ejector.

A second invention of the present invention is a method for vacuum distillation of an easily polymerizable compound using a steam ejector, which comprises a step of heating an outer surface of the steam ejector.

The easily polymerizable compound in the second invention is preferably an acrylic acid or an acrylic ester and is preferably an acrylic acid resulting from gas-phase catalytic oxidation using propane, propylene, or acrolein as a material.

Furthermore, the outer surface of the steam ejector is preferably heated using a steam trace and is preferably heated using an electro-thermal heater.

Furthermore, the outer surface of the steam ejector is preferably heated to 50° C. or higher.

Furthermore, the steam ejector preferably has a multistage configuration, and a liquid seal vacuum pump is preferably arranged downstream of the steam ejector.

Advantageous Effects of Invention

According to the present invention, it is possible to provide a method in which, when a steam ejector is used as a decompression apparatus for a vacuum distillation process for an easily polymerizable compound, the steam ejector is prevented from being occluded due to polymerization of the easily polymerizable compound. Further it is possible to provide a method for manufacturing an acrylic acid that is an easily polymerizable compound, using the above-described method.

DESCRIPTION OF EMBODIMENTS

Figure 1:
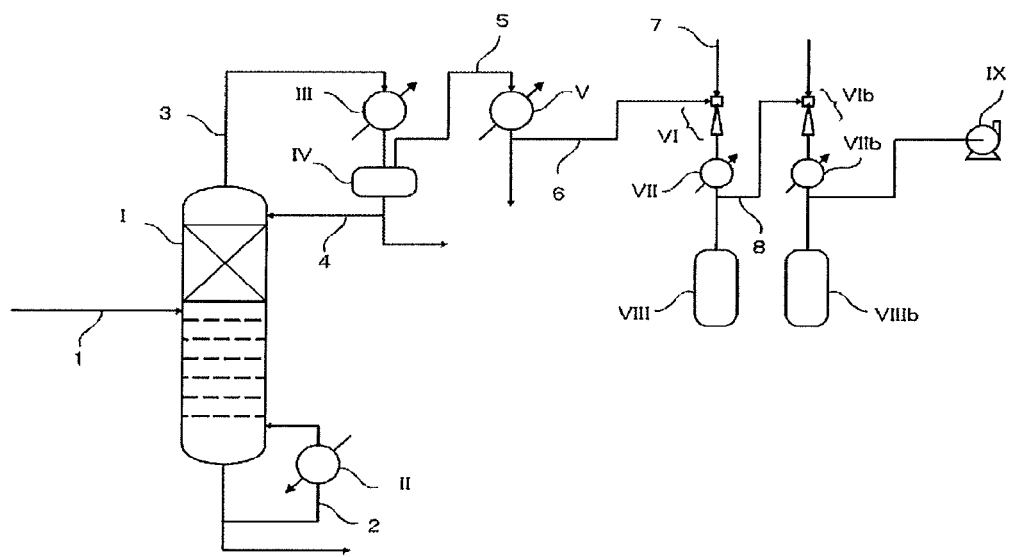
FIG. 1 is a diagram depicting an example of a vacuum distillation method in the present invention.

A method in the present invention will be described in detail based on the attached drawings. FIG. 1 is a flow sheet depicting an example of a vacuum distillation method in the present invention.

A material (1) is a crude-polymerizable-compound-containing liquid containing an easily polymerizable compound, and is supplied to a distillation column (I). Examples of the easily polymerizable compound include acrylic acids, methacrylic acids, and styrenes.

The acrylic acids generally cover acrylic acids and acrylic esters resulting from combinations of the acrylic acids and alcohol and refer to at least one of the acrylic acids and the acrylic esters. Examples of the acrylic acids include an acrylic acid, methyl acrylate, ethyl acrylate, butyl acrylate, isobutyl acrylate, tertiary butyl acrylate, and methoxyethyl acrylate. The acrylic acid preferably results from gas-phase catalytic oxidation using propane, propylene, or acrolein as a material.

Furthermore, the methacrylic acids generally cover methacrylic acids and methacrylate esters resulting from combinations of the methacrylic acids and alcohol and refer to at least one of the methacrylic acids and the methacrylate esters. Examples of the methacrylic acids include a methacrylic acid, methyl methacrylate, ethyl methacrylate, and butyl methacrylate.

Furthermore, the styrenes generally cover styrenes and styrene compounds having a replacement group and refer to at least one of the styrenes and the styrene compounds. Examples of the styrenes include styrene, α-methylstyrene, parachlorostyrene, and paramethoxystyrene.

Examples of the type of the distillation column include a tray column, a packed column, or a combination thereof (a packed column and a tray column, a plurality of types of tray columns, a plurality of types of packed columns).

Examples of the type of the tray column include the most general-purpose sieve tray, and a dual flow tray, a disk and donut tray, and a turbo grid tray which have no downcomer and few areas where the liquid and the gas are stagnant.

The tray column, having few stagnant areas, is advantageously unlikely to be occluded with polymers. However, the tray column is, due to the simple structure thereof, likely to be inefficient in gas-liquid contact and thus preferably has a multistage configuration. In this case, in order to provide a number of theoretical plates needed for distillation and separation, the number of the trays in the column normally has three or more, preferably five or more, and more preferably ten or more. On the other hand, with an increased number of trays, the gas concentrates in a central portion of the column, whereas the liquid concentrates on an outer side of the column, reducing the efficiency of gas-liquid contact. Consequently, the number of the trays is normally 60 or less, preferably 40 or less, and more preferably 30 or less.

Packings used for the packed column are roughly classified into structured packings and random packings.

Examples of the structured packing include guaze structured packings such as Sulzer packing (manufactured by Sulzer Chemtech Ltd.) and Techno-pack (manufactured by Sanrei Techno Corporation), sheet structured packings such as Mellapack (manufactured by Sulzer Chemtech Ltd.), Techno-pack (manufactured by Sanrei Techno Corporation), and MC pack (manufactured by Mitsubishi Chemical Engineering Corporation), and grid structured packings such as Felxigrid (manufactured by Koch-Glitsch Inc.). Other examples include Goodroll Packing that is bundled and knitted metal wires (manufactured by TO-TOKU Engineering Corporation) and Super H Pack in which a large number of metal wires are vertically arranged (manufactured by Nagaoka CO., LTD.).

Furthermore, examples of the random packing include a cascade mini ring, IMTP, Interlox (manufactured by Koch-Glitsch Inc.), Teralet (manufactured by Tukishima Kankyo Engineering Ltd.), and Flexiring (manufactured by JGC Corporation).

A portion of the liquid extracted from a bottom of the distillation column (I) is fed to a reboiler (II), where the portion is heated and then returned to the distillation column (I).

Examples of the reboiler (II) include a multitubular heat exchanger and a spiral heat exchanger. A thin-film evaporator may be used instead of or along with the reboiler.

To prevent polymerization in the distillation column, a polymerization inhibitor or a polymerization inhibitor solution is fed though a feed solution, a reflux, or an intermediate portion of the distillation column.

Examples of the polymerization inhibitor used include phenol compounds such as hydroquinone and methoxyphenol, a copper or manganese complex of a dialkyl dithiocarbamic acid such as a 2, 2-dibutyl dithiocarbamic acid, a nitroxyl radical compound such as 4-hydroxy-2, 2, 6, 6-tetramethylpyridyl oxide, and phenothiazine. For a similar purpose, an oxygen-containing gas such as air or nitrogen-diluted air is supplied. The oxygen-containing gas is also used as a purge gas allowing instrumentation devices such as a pressure gauge to be protected from a process fluid in the column.

An overhead distillate gas (3) from the distillation column (I) is condensed in a condenser (III), and the resultant gas is transferred to a drum (IV). A portion of a condensate in the drum (IV) may be circulated to the distillation column (I) as a reflux (4). The condenser (III) is commonly cooled by air or water and can be cooled down to a temperature close to the temperature of the outside air, a river, sea water, or the like to which heat is directly or indirectly discharged.

Uncondensed components (5) in the condenser (III) are further condensed in a vent condenser (V). The uncondensed components (5) are a low-boiling-point component contained in the feed solution (1) to the distillation column (I), an oxygen-containing gas supplied to the distillation column in order to prevent polymerization, a purge gas to the instrumentation devices, the outside air entering negative-pressure apparatuses through connection portions such as flanges, and the like. A refrigerant in the vent condenser (V) is commonly regulated by a refrigerator or the like. However, cold waste heat from a process, for example, heat resulting from volatilization of a liquefied gas or melting of a crystallized solid, may be used directly or indirectly as a refrigerant. If the uncondensed components (5) are not substantially condensed by the further cooling, the vent condenser (V) may not be used.

Uncondensed components (6) in the vent condenser (V) or the uncondensed components (5) in the condenser (III) in the case where the vent condenser (V) is not used are guided to an inlet port of the steam ejector (VI) that is a decompression apparatus. Decompression is performed to reduce the bottom temperature of the distillation column (I). Thus, if a large pressure loss occurs in the distillation column, the pressure needs to be further reduced using the steam ejector (VI).

To prevent polymerization, the bottom temperature of the distillation column (I) is preferably lower. However, a reduced pressure leads to an increased size of the distillation column, or a reduced condensation temperature of a distilled gas precludes condensation in the condenser (III), increasing the rate of condensation in the vent condenser (V). For these and other reasons, excessive decompression significantly degrades economic performance and is not preferable. Thus, preferably, the amount of condensation in the condenser (III) is at least larger than the amount of condensation in the vent condenser (V).

In order to suppress polymerization resulting from generation of radicals, the bottom temperature of the distillation column is preferably equal to or lower than the boiling point of the compound under normal pressure and more preferably at least 10° C. lower than the boiling point.

For the acrylic acid, included in the easily polymerizable compounds, the bottom temperature is preferably 100° C. or lower and more preferably 90° C. or lower. For the acrylic ester, the boiling point varies significantly according to the type of the acrylic ester, precluding the bottom temperature to be determined using the same numerical range. However, to suppress polymerization as described above, the bottom temperature is preferably 10 to 100° C. and more preferably 15 to 90° C. lower than the boiling point of the acrylic acids under normal pressure.

Furthermore, for the methyl methacrylate, included in the easily polymerizable compounds, the bottom temperature is preferably 95° C. or lower and more preferably 85° C. or lower.

Furthermore, for the styrene, included in the easily polymerizable compounds, the bottom temperature is preferably 130° C. or lower and more preferably 115° C. or lower.

When an in-column gas is extracted through a portion of the distillation column (III) other than an overhead portion thereof (not depicted in the drawings), a distillate gas is condensed using a condenser different from the condenser for the overhead portion and the vent condenser. Then, uncondensed components are guided to the inlet port of the steam ejector.

The uncondensed components (6) sucked into the steam ejector (VI) is discharged through an outlet of the steam ejector (VI) along with the driving steam (7). The driving steam (7) is at a pressure of approximately 0.5 to 2 MPaG and is in an overheated state where the driving stream is several to several tens of degrees centigrade higher than a saturation temperature. Steam at a lower pressure may allow driving to be achieved but is not economical due to the need for a substantially increased amount of such steam. Steam at a higher pressure is more efficient but requires equipment and piping to demonstrate high pressure resistance performance, thus degrading economic performance in terms of capital investment. A discharged mixed gas is cooled in the condenser (VII), and the condensed gas is stored in a vessel (VIII). In particular, when a liquid temperature in the vessel (VIII) is 40° C. or higher and/or the concentration of the easily polymerizable compound in the liquid in the vessel is high, a polymerization inhibitor may be added to the stored gas.

The uncondensed components (8) in the condenser (VII) are fed to a discharged gas treatment facility or further fed to an inlet port of a steam ejector (VIb) or a liquid seal vacuum pump (IX) as needed. When the steam ejector used has a multistage configuration, cooling a mixed gas discharged from an ejector at the first stage to condense a portion of the mixed gas reduces the amount of gas sucked into ejectors at the second and subsequent stages and is efficient. However, the number of pieces of equipment increases, and the condensation temperature may be lower than the outside temperature depending on conditions. For these and other reasons, the mixed gas discharged from the ejector may be sucked into the next ejector without being cooled or condensed.

Furthermore, the liquid seal vacuum pump is not suitable for high vacuum because a sealing liquid has a vapor pressure and because the capacity of the vacuum pump depends on the volume of a sucked gas, but is suitable for a state with a relatively low vacuum. Thus, the liquid seal vacuum pump is preferably arranged downstream of the steam ejector. Furthermore, when the steam ejector used has a multistage configuration, then in an aspect, the liquid seal vacuum pump is arranged downstream of the steam ejector at the final stage.

Now, the steam ejector will be described.

Figure 2:
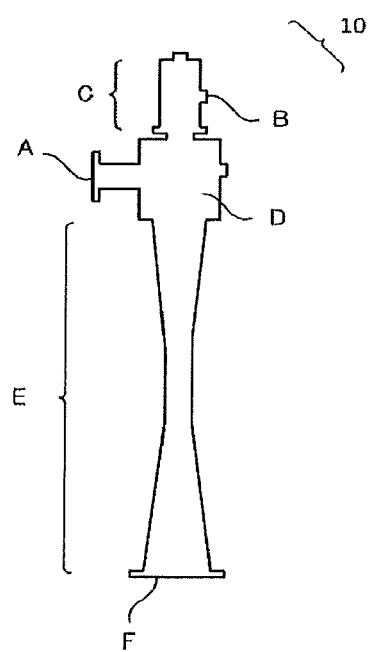
FIG. 2 is a diagram depicting an example of a steam ejector in the present invention.

FIG. 2 is an example of a steam ejector (10). The steam ejector (10) includes an inlet port (A) through which the uncondensed components (6) from the vent condenser (V) is sucked, a supply port (B) for the driving steam, a steam chamber (C), a vacuum chamber (D), a steam nozzle (not depicted in the drawings) in the vacuum chamber (D), a diffuser (E), and an outlet (F) for the mixed gas of the uncondensed components and the steam.

In an aspect, a single steam ejector is provided when a compression ratio is low. On the other hand, the amount of driving steam needed increases rapidly with the compression ratio. Thus, in an aspect, a multistage configuration is provided to reduce the consumption of driving steam when the compression ratio is high. However, an excessive increase in the number of stages is undesirable due to a resultant increase in the number of additional facilities such as condensers. In view of these points, the appropriate number of stages for the steam ejector is one to four.

The present invention is characterized in that an outer surface of the steam ejector is heated. A heated area is preferably an outer surface of the inlet port (A) and an outer surface of the vacuum chamber (D) and more preferably these outer surfaces and an outer surface of the diffuser (E).

When a multistage steam ejector is used, since the concentration of the easily polymerizable compound contained in the sucked gas increases as it moves upstream, normally, the outer surface of the steam ejector at at least the first stage is heated, and preferably, the outer surfaces of as many steam ejectors as possible from the upstream side are heated. More preferably, the outer surfaces of all the steam ejectors are heated.

A preferable temperature range based on heating is such that the outer surface of the steam ejector is normally heated to have an outer surface temperature of 50° C. or higher, preferably 60° C. or higher, and more preferably 70° C. or higher, based on actual performance.

The outer surface temperature of the steam ejector means the lowest of the temperatures of the outer surfaces of the inlet port, the vacuum chamber, and the diffuser in the steam ejector. Points where the temperature is measured do not include points such as a flange portion and a strut welded to a junction with a support member which are located at a distance of longer than 25 mm from a space inside the steam ejector. The temperature can be measured by, for example, inserting a thermometer through a gap in or an end of a constructed heating source or using a non-contact thermometer such as a radiation thermometer.

On the other hand, the sucked gas has its volume increased consistently with the temperature to increase loads on the steam ejector. Consequently, when no problem such as polymerization is expected to be posed, since a lower temperature is more preferable, the outer surface temperature of the steam ejector is normally lower than 150° C., preferably 140° C. or lower, and more preferably 130° C. or lower.

A heating method is not particularly limited. For example, a steam pipe (steam trace) may be wound around the steam ejector or a heating wire of an electro-thermal heater may be wound around the steam ejector. At this time, the hearting wire of the electro-thermal heater is preferably wound around the steam ejector because this enables strict temperature control. More preferably, the steam trace is wound around the steam ejector because this allows a heat source to be easily obtained and facilitates temperature control.

Figure 3:
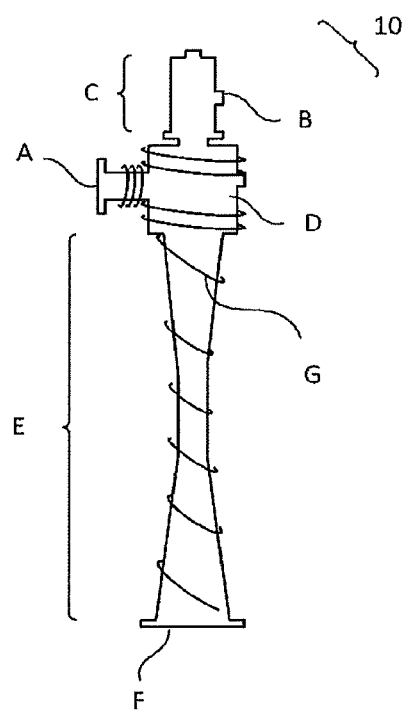
FIG. 3 is a diagram depicting an example of a method for heating an outer surface of the steam ejector in the present invention.

A winding method is also not particularly limited. For example, one steam trace or one heating wire of a ribbon-like electro-thermal heater may be wound around the steam ejector as depicted in FIG. 3, or several steam traces or heating wires may be wound around the steam ejector. Furthermore, the pipes of the stream traces or the heating wires of the ribbon-like electro-thermal heat may be spaced from one another as depicted in FIG. 3 or may not be spaced from one another. In other words, any method may be used as long as the method allows the outer surface of the steam ejector to be heated to the predetermined temperature.

As a heat source for the steam trace, the driving steam in the steam ejector can be split into fractions. However, steam at a lower pressure fed through a different line is preferably used in view of operational management and maintenance.

The outer surface of the steam ejector may be heated before an operation period for the steam ejector. Furthermore, the outer surface preferably continues to be heated during the operation period for the steam ejector. However, even if heating of the outer surface is temporarily suspended for any reason, the effects of the present invention are prevented from being lost.

EXAMPLES

The present invention will be described in detail in conjunction with examples. However, the scope of the present invention is not limited to the examples.

Comparative Example 1

An acrylic-acid-containing gas resulting from gas-phase catalytic oxidation of propylene was collected in a solvent. The solvent was then distilled and separated to obtain a crude acrylic acid having an acrylic-acid concentration of 99% or more and containing phenothiazine and dibutyl dithiocarbamic acid copper as a polymerization inhibitor. The crude acrylic acid was supplied to the distillation column. A random packed column packed with IMTP was used as the distillation column. When the distillation column was operated at an overhead pressure of 2.8 kPa, an overhead temperature of 52° C., and a reflux ratio of 1.2, a liquid temperature in a reflux vessel was 28° C. and a bottom temperature was 72° C. Methoquinone was supplied to an overhead condenser and a reflux line as a polymerization inhibitor. Furthermore, nitrogen-diluted air was supplied through the bottom in order to prevent polymerization.

Cold water at 16° C. was supplied as a refrigerant to the vent condenser, and uncondensed components were guided to the inlet port of the steam ejector at the first stage. In Comparative Example 1, as the steam ejector, such a steam ejector as depicted in FIG. 2 was used. A gas pipe from the vent condenser to the steam ejector was kept at an appropriate temperature using a steam trace or a heat insulating material. Air was fed to the middle of the gas pipe while being controlled using a control valve (CV), so as to keep the overhead pressure of the distillation column constant. A mixed exhaust gas from the steam ejector was cooled in a two-stage heat exchanger using cooling water at 28° C. and cooling water at 16° C. Then, uncondensed components were guided to the inlet port of the steam ejector at the second stage. A mixed exhaust gas from the steam ejector was cooled in the heat exchanger using cooling water at 28° C. Uncondensed components were guided to the inlet port of the liquid seal vacuum pump. Driving steam in the steam ejector was at 1.2 MPaG both at the first stage and at the second stage.

While the distillation column was operated for 11 months under the above-described conditions, the steam ejector walls switched to a spare three times for cleaning. Three weeks to two months after the cleaning of the steam ejector, and on average, 1.5 months after the cleaning, a clear decrease in a CV opening angle except for a fluctuation in operation and the like was observed, in other words, a decrease in the amount of air supplied for pressure adjustment which decrease resulted from a decrease in a suction force of the steam ejector. A variation in CV opening angle resulting from a fluctuation in operation was 1 to 7%.

When the operation was continued, the outer surface temperature of the inlet port of the steam ejector at the first stage was checked using a radiation thermometer. Then, the temperature was 40 to 46° C. This is definitely higher than the temperature of the uncondensed components in the vent condenser. A temperature at least higher than the dew point of a sucked gas is considered to have been maintained.

Referential Example 1

The distillation column was operated in the same manner as that in Comparative Example 1 except that the driving steam in the steam ejector was at 1.0 MPaG. A duration after cleaning of the steam ejector and before a decrease in CV opening angle was three weeks and five weeks, exhibiting no improvement.

Example 1

Example 1 was similar to the above-described Comparative Example 1 except that the steam ejector was operated with the outer surface of the inlet port, the outer surface of the vacuum portion, and the outer surface of the diffuser of the steam ejector at the first stage and the second stage heated using a steam trace as depicted in FIG. 3. Steam used for the steam trace was at 0.3 MPaG. The outer surface temperature of the inlet port of the steam ejector was 70 to 85° C. During eleven months of continuous operation, no definite decrease in CV opening angle was observed. When the operation was continued for six months, the steam for the trace was stopped for two days with the pipe of the steam trace remaining unchanged. Then, supply of steam was resumed. No significant difference was observed between a state before the resumption and a state after the resumption. As described above, heating the outer surface of the steam ejector has been clarified to be particularly effective for a long continuance of operation, and relatively short stoppage of heating has been clarified to be possible.

While the invention has been described in detail and with reference to specific embodiments thereof, it will be apparent to one skilled in the art that various changes and modifications can be made therein without departing from the spirit and scope thereof.

REFERENCE SIGNS LIST

1 Material
2 Column bottom liquid
3 Column top distillate gas
4 Reflux
5, 6, 8 Uncondensed components
7 Driving steam
I Distillation column
II Reboiler
III, VII, VIIb Condenser
IV Drum
V Vent condenser
10, VI, VIb Steam ejector
VIII, VIIIb Vessel
IX Liquid seal vacuum pump
A Inlet port
B Supply port
C Steam chamber
D Vacuum chamber
E Diffuser
F Outlet
G Steam trace

The invention claimed is:

1. A method for manufacturing an acrylic acid, comprising:
executing vacuum distillation, using a steam ejector, on an acrylic acid resulting from gas-phase catalytic oxidation using propane, propylene, or acrolein as a material,
wherein an outer surface of the steam ejector is heated during the vacuum distillation, and
the vacuum distillation is executed such that the driving steam discharged through the outlet of the steam ejector has a pressure of from 0.5 to 2 MPaG.

2. The method according to claim 1, wherein the outer surface of the steam ejector is heated by using a steam trace.

3. The method according to claim 1, wherein the outer surface of the steam ejector is heated by using an electro-thermal heater.

4. The method according to claim 1, wherein the outer surface of the steam ejector is heated to 50° C. or higher.

5. The method according to claim 1, wherein the steam ejector has a multistage configuration.

6. The method according to claim 1, wherein a liquid seal vacuum pump is arranged downstream of the steam ejector.

7. A method for vacuum distillation of an easily polymerizable compound using a steam ejector, comprising:
heating an outer surface of the steam ejector; and
controlling a pressure of the driving steam discharged through the outlet of the steam ejector to be from 0.5 to 2 MPaG.

8. The method according to claim 7, wherein the easily polymerizable compound is an acrylic acid or an acrylic ester.

9. The method according to claim 8, wherein the easily polymerizable compound is an acrylic acid resulting from gas-phase catalytic oxidation using propane, propylene, or acrolein as a material.

10. The method according to claim 7, wherein the outer surface of the steam ejector is heated by using a steam trace.

11. The method according to claim 7, wherein the outer surface of the steam ejector is heated by using an electro-thermal heater.

12. The method according to claim 7, wherein the outer surface of the steam ejector is heated to 50° C. or higher.

13. The method according to claim 7, wherein the steam ejector has a multistage configuration.

14. The method according to claim 7, wherein a liquid seal vacuum pump is arranged downstream of the steam ejector.

15. The method according to claim 7, wherein the heating and the controlling are simultaneously carried out.

16. The method according to claim 1, wherein the steam ejector is heated to 50° C. or higher and lower than 150° C.

17. The method according to claim 1, wherein the steam ejector is heated to 70° C. or higher and 130° C. or lower.

18. The method according to claim 1, wherein gas entering the inlet port of the steam ejector consists of an exhaust gas from a condenser positioned upstream of the steam ejector.

19. The method according to claim 1, further comprising:
introducing gas comprising the easily polymerizable compound to the inlet port of the steam ejector such that the gas entering the inlet port consists of an exhaust gas from a condenser positioned upstream of the steam ejector.

20. The method according to claim 8, wherein the outer surface of the steam ejector is heated to 50° C. or higher.

* * * * *